(12) United States Patent
Chowaniec et al.

(10) Patent No.: US 11,839,441 B2
(45) Date of Patent: Dec. 12, 2023

(54) ROBOTIC SURGICAL SYSTEM WITH AUTOMATED GUIDANCE

(71) Applicant: Covidien LP, Mansfield, MA (US)

(72) Inventors: Matthew Chowaniec, Madison, CT (US); Xingrui Chen, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 1057 days.

(21) Appl. No.: 16/615,226

(22) PCT Filed: May 7, 2018

(86) PCT No.: PCT/US2018/031302
§ 371 (c)(1),
(2) Date: Nov. 20, 2019

(87) PCT Pub. No.: WO2018/217431
PCT Pub. Date: Nov. 29, 2018

(65) Prior Publication Data
US 2020/0163730 A1 May 28, 2020

Related U.S. Application Data

(60) Provisional application No. 62/510,938, filed on May 25, 2017.

(51) Int. Cl.
*A61B 34/32* (2016.01)
*A61B 90/00* (2016.01)
*A61B 34/30* (2016.01)

(52) U.S. Cl.
CPC .............. *A61B 34/32* (2016.02); *A61B 90/36* (2016.02); *A61B 2034/301* (2016.02); *A61B 2034/302* (2016.02); *A61B 2090/363* (2016.02)

(58) Field of Classification Search
CPC ... A61B 34/32; A61B 90/36; A61B 2034/301; A61B 2034/302; A61B 2090/363; A61B 34/20; A61B 90/39; A61B 2090/3979
See application file for complete search history.

(56) References Cited

U.S. PATENT DOCUMENTS 5,868,673 A 2/1999 Vesely
6,132,368 A 10/2000 Cooper
(Continued)

FOREIGN PATENT DOCUMENTS

CN 102905642 A 1/2013
DE 102010029275 A1 12/2011
(Continued)

OTHER PUBLICATIONS

Japanese Office Action dated Jan. 26, 2022 corresponding to counterpart Patent Application JP 2019-564842.
(Continued)

*Primary Examiner* — Jeff A Burke
*Assistant Examiner* — Sihar A Karwan
(74) *Attorney, Agent, or Firm* — CARTER, DELUCA & FARRELL LLP

(57) ABSTRACT

A robotic surgical system includes at least one robot arm, at least one instrument, and a plurality of drive motors configured to drive the at least one robot arm and at least one instrument. The system also includes a laparoscopic port having a plurality of fiducials, a sensor configured to detect the plurality of fiducials, and a controller configured to control the plurality of drive motors. The controller includes a processor that determines a current distance between each fiducial among the plurality of fiducials, determines a location of the laparoscopic port based on the distance between each fiducial, determines a position of the at least one robot arm and the at least one instrument relative to the location
(Continued)

of the laparoscopic port, and controls the plurality of drive motors to align the at least one robot arm or the at least one instrument with the laparoscopic port.

19 Claims, 5 Drawing Sheets

(56) References Cited

U.S. PATENT DOCUMENTS

| | | |
|---|---|---|
| 6,206,903 B1 | 3/2001 | Ramans |
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll et al. |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco et al. |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez et al. |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,082,064 B2 | 12/2011 | Kay |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |

(56) References Cited

U.S. PATENT DOCUMENTS

| | | |
|---|---|---|
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | O |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,280,158 B2 | 3/2016 | Bron et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,358,682 B2 | 6/2016 | Ruiz Morales |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,116 B2 * | 7/2019 | Boctor .............. A61B 34/30 |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |

(56) References Cited

U.S. PATENT DOCUMENTS

| | | |
|---|---|---|
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2003/0120283 A1 | 6/2003 | Stoianovici et al. |
| 2010/0241079 A1 | 9/2010 | Abrams |
| 2013/0066335 A1 | 3/2013 | Barwinkel et al. |
| 2014/0276007 A1 | 9/2014 | Sela et al. |
| 2016/0235493 A1 | 8/2016 | LeBoeuf, II et al. |
| 2017/0007349 A1 | 1/2017 | Solar et al. |
| 2017/0079722 A1* | 3/2017 | O'Grady .............. A61B 90/96 |
| 2017/0165005 A1 | 6/2017 | Kheradpir et al. |

FOREIGN PATENT DOCUMENTS

| | | |
|---|---|---|
| DE | 102010040987 A1 | 3/2012 |
| JP | 2015150636 A | 8/2015 |
| WO | 2015129474 A1 | 9/2015 |
| WO | 2016013636 A1 | 1/2016 |
| WO | 2016029289 A1 | 3/2016 |

OTHER PUBLICATIONS

Indian Office Action dated Mar. 2, 2022 corresponding to counterpart Patent Application IN 201917050301.
Chinese First Office Action dated May 7, 2022 corresponding to counterpart Patent Application CN 201880034162.3.
International Search Report dated Sep. 3, 2018 and Written Opinion completed Aug. 29, 2018 corresponding to counterpart Int'l Patent Application PCT/US18/31302.
Extended European Search Report dated Feb. 9, 2021 corresponding to counterpart Patent Application EP 18806526.2.
Weiss et al: "Dynamic Sensor-Based Control of Robots with Visual Feedback", IEEE Journal on Robotics and Automation, IEEE, USA, vol. 3, No. 5, Oct. 1, 1987 (Oct. 1, 1987), pp. 404-417, XP011217419, ISSN: 0882-4967, DOI: 10.1109/JRA.1987.1087115.

* cited by examiner

ROBOTIC SURGICAL SYSTEM WITH AUTOMATED GUIDANCE

CROSS-REFERENCE TO RELATED APPLICATIONS

This application is a National Stage Application of PCT/US2018/031302, filed May 7, 2018 under 35USC § 371 (a), which claims benefit of and priority to U.S. Provisional Patent Application Ser. No. 62/510,938 filed May 25, 2017, the disclosures of each of the above-identified applications are hereby incorporated by reference in their entirety.

BACKGROUND

Robotic surgical systems such as teleoperative systems are used to perform minimally invasive surgical procedures that offer many benefits over traditional open surgery techniques, including less pain, shorter hospital stays, quicker return to normal activities, minimal scarring, reduced recovery time, and less injury to tissue.

Robotic surgical systems can have a number of robotic arms that move attached instruments or tools, such as an image capturing device, a stapler, an electrosurgical instrument, etc., in response to movement of input devices by a surgeon viewing images captured by the image capturing device of a surgical site. During a surgical procedure, each of the tools may be inserted through an opening, e.g., a laparoscopic port, into the patient and positioned to manipulate tissue at a surgical site. The openings are placed about the patient's body so that the surgical instruments may be used to cooperatively perform the surgical procedure and the image capturing device may view the surgical site.

During the surgical procedure, the tools are manipulated in multiple degrees of freedom by a clinician. In order to manipulate the tool through the laparoscopic port, the clinician has to position the robotic arm correctly to facilitate insertion and/or removal of the tool. However, obtaining the correct position may be a relatively time consuming step. Further, manual positioning of the robotic arm by the clinician adds further time and complexity to this step of the surgical procedure.

Accordingly, there is a need for guiding the robotic arms of the robotic surgical system to reduce the complexity and duration of a surgical procedure, as well as increase the outcome and/or results of the surgical procedure.

SUMMARY

The present disclosure relates generally to guiding of a robotic surgical system and, in particular, guiding a robotic arm of the robotic surgical system to automatically insert and/or remove tools through an opening or laparoscopic port.

In an aspect of the present disclosure, a robotic surgical system is provided. The system includes at least one robot arm, at least one instrument coupled to the robot arm, and a plurality of drive motors configured to drive the at least one robot arm and at least one instrument. The system also includes a laparoscopic port having a plurality of fiducials and a sensor configured to detect the plurality of fiducials. A controller that is configured to control the plurality of drive motors includes a processor configured to determine a current distance between each fiducial among the plurality of fiducials, determine a location of the laparoscopic port based on the distance between each fiducial, determine a position of the at least one robot arm and the at least one instrument relative to the location of the laparoscopic port, and control the plurality of drive motors to align the at least one robot arm or the at least one instrument with the laparoscopic port.

In embodiments, the processor is also configured to obtain a predetermined distance between each fiducial among the plurality of fiducials and obtain a predetermined distance between each fiducial and the laparoscopic port. The processor may determine the location of the laparoscopic port based on the current distance between each fiducial among the plurality of fiducials, the predetermined distance between each fiducial among the plurality of fiducials, and the predetermined distance between each fiducial and the laparoscopic port.

In embodiments, the processor is configured to obtains a length of the at least one instrument and a length of the at least one robot arm. Control of the plurality of drive motors may be based on the position of the at least one robot arm and the at least one instrument relative to the location of the laparoscopic port, the length of the at least one instrument, and the length of the at least one robot arm.

In some embodiments, the plurality of fiducials is active light emitting diodes.

In some embodiments, the robotic surgical system includes a light source configured to emit light directed at the plurality of fiducials. The plurality of fiducials may include a reflective material and the light emitted from the light source may be reflected by the plurality of fiducials and detected by the sensor.

In another aspect of the present disclosure, a method for guiding a robot arm and/or instrument toward a laparoscopic port is provided. The method includes determining a current distance between each fiducial among a plurality of fiducials disposed around the laparoscopic port and determining a location of the laparoscopic port based on the distance between each fiducial. The method also includes determining a position of the robot arm and the instrument relative to the location of the laparoscopic port and controlling a plurality of drive motors associated with the robot arm and the instrument to align the robot arm or the instrument with the laparoscopic port.

In embodiments, the method includes obtaining a predetermined distance between each fiducial among the plurality of fiducials and obtaining a predetermined distance between each fiducial and the laparoscopic port. The method also includes determining the location of the laparoscopic port based on the current distance between each fiducial among the plurality of fiducials, the predetermined distance between each fiducial among the plurality of fiducials, and the predetermined distance between each fiducial and the laparoscopic port.

In embodiments, the method includes obtaining a length of the instrument and obtaining a length of the robot arm. Controlling the plurality of drive motors is based on the position of the robot arm and the instrument relative to the location of the laparoscopic port, the length of the instrument, and the length of the robot arm.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

The present disclosure is directed to systems and methods for guiding one or more robotic arms in a robotic surgical system utilizing images captured during a surgical procedure. Image data captured during a surgical procedure may be analyzed to guide a robotic arm having a device or tool coupled thereto to insert and/or remove the tool from a laparoscopic port. In the systems described herein, one or more laparoscopic ports have three (3) fiducials, e.g., active infrared light emitting diodes (LEDs), with known distances between the fiducials and known distances between the fiducials and a center of the laparoscopic port. The positions of each fiducial may be analyzed using motion analyzing techniques to establish a plane defined by the fiducials and establish the steps necessary to move the robot arm in position. The position of the center of the laparoscopic port relative to the three (3) fiducials determines where to insert and/or remove the tool, and an orientation angle for the tool.

In the systems described herein, aligning and orienting the robotic arm to insert and/or remove the tool through the laparoscopic port relies on one or more variables. The variable(s) may include, but is/are not limited to, distance(s) between three (3) or more fiducials, distance(s) between the fiducials and the center of the laparoscopic port, the port plane defined by the fiducials, and/or the length of the interchangeable tool and robotic arm.

The systems described herein permit quicker installation of robotic instrumentation into laparoscopic ports, less intervention on the part of a clinician during a surgical procedure, and/or potentially lower incidents of impact with a laparoscopic port site.

Figure 1:
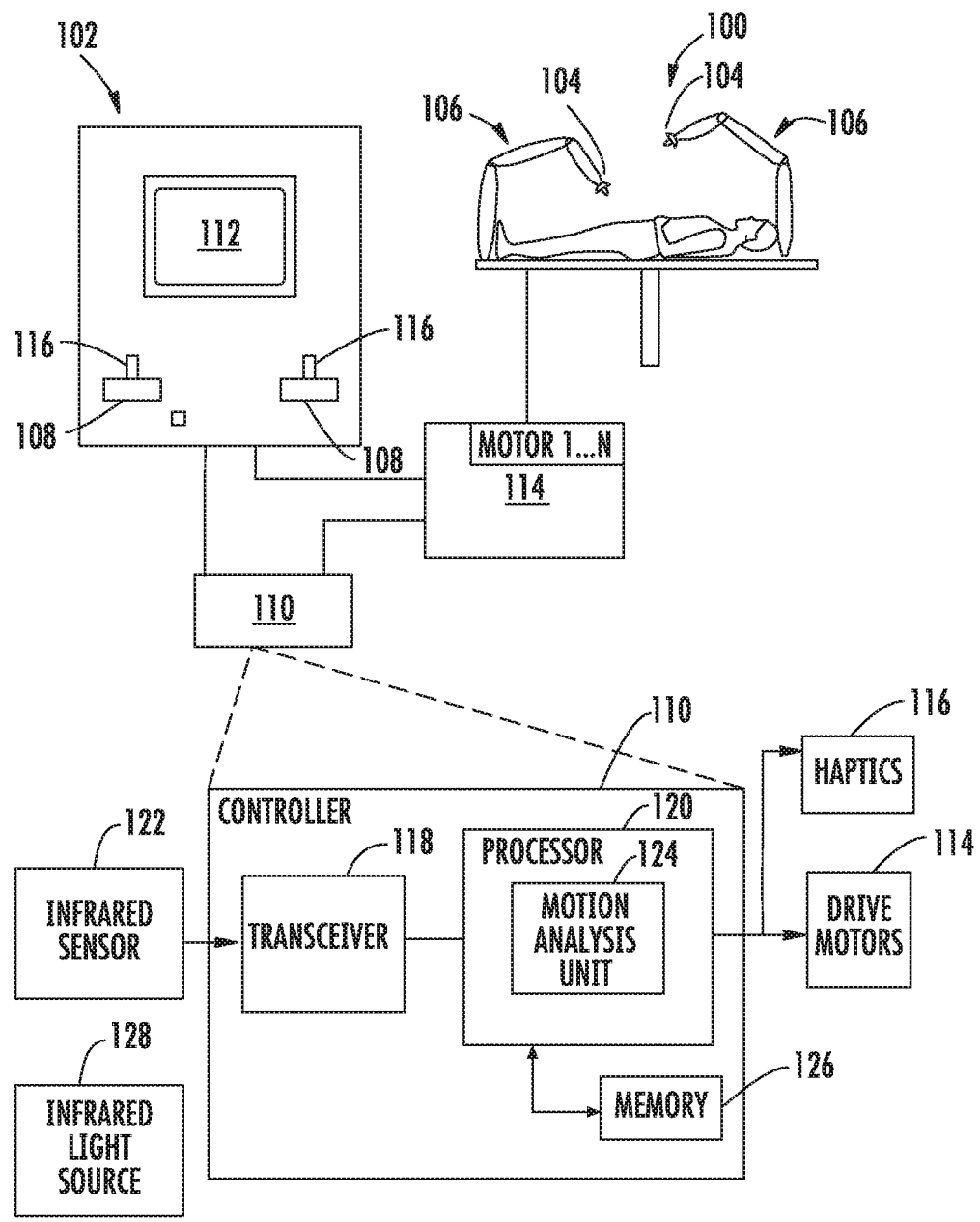
FIG. 1 is a schematic illustration of a user interface and a robotic system of a robotic surgical system in accordance with the present disclosure.

Turning to FIG. 1, a robotic surgical system 100 may be employed with one or more consoles 102 that are next to the operating theater or located in a remote location. In this instance, one team of clinicians or nurses may prep the patient for surgery and configure the robotic surgical system 100 with one or more tools 104 while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

The robotic arms 106 of the surgical system 100 are typically coupled to a pair of master handles 108 by a controller 110. Controller 110 may be integrated with the console 102 or provided as a standalone device within the operating theater. The handles 106 can be moved by the clinician to produce a corresponding movement of the working ends of any type of tools 104 (e.g., probes, mechanical or electrosurgical end effectors, graspers, knifes, scissors, etc.) attached to the robotic arms 106. For example, tool 104 may be a probe that includes an image capture device.

The console 102 includes a display device 112 which is configured to display two-dimensional or three-dimensional images. The display device 112 displays the images of the surgical site which may include data captured by tool 104 positioned on the ends 114 of the arms 106 and/or include data captured by imaging devices that are positioned about the surgical theater (e.g., an imaging device positioned within the surgical site, an imaging device positioned adjacent the patient, imaging device positioned at a distal end of an imaging arm). The imaging devices may capture visual images, infra-red images, ultrasound images, X-ray images, thermal images, and/or any other known real-time images of the surgical site. The imaging devices transmit captured imaging data to the controller 110 which creates the images of the surgical site in real-time from the imaging data and transmits the images to the display device 112 for display.

The movement of the master handles 108 may be scaled so that the working ends have a corresponding movement that is different, smaller or larger, than the movement performed by the operating hands of the clinician. The scale factor or gearing ratio may be adjustable so that the operator can control the resolution of the working ends of the surgical instrument(s) 104.

During operation of the surgical system 100, the master handles 108 are operated by a clinician to produce a corresponding movement of the robotic arms 106 and/or surgical instruments 104. The master handles 108 provide a signal to the controller 110 which then provides a corresponding signal to one or more drive motors 114. The one or more drive motors 114 are coupled to the robotic arms 106 in order to move the robotic arms 106 and/or surgical instruments 104.

The master handles 108 may include various haptics 116 to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such haptics 116 provide the clinician with enhanced tactile feedback simulating actual operating conditions. The haptics 116 may include vibratory motors, electroactive polymers, piezoelectric devices, electrostatic devices, subsonic audio wave surface actuation devices, reverse-electrovibration, or any other device capable of providing a tactile feedback to a user. The master handles 108 may also include a variety of different actuators (not shown) for delicate tissue manipulation or treatment further enhancing the clinician's ability to mimic actual operating conditions.

The controller 110 includes a transceiver 118 and a processor 120. Transceiver 118 receives a signal from infrared sensors 122 which will be described in more detail below. The signal from infrared sensors may be transmitted to transceiver 118 via any conventional wired or wireless methods. Transceiver 118 provides the signal to a motion analysis unit 124 in processor 120 which performs a motion analysis on the signal in order to control the one or more drive motors 114 to move the robotic arms 106 and/or surgical instruments 104 into the correct position and/or orientation. A memory 126 may store an algorithm used to perform the motion analysis. In some embodiments, memory 126 may store a look up table (LUT) that includes information pertaining to instruments 104, robot arms 106, and laparoscopic ports discussed below.

As will be discussed in more detail below, infrared sensors receive light from infrared light sources. The infrared sensors may be disposed on the robotic arm 106, the surgical instrument 104, the laparoscopic port 130, or may be disposed anywhere in the surgical environment. The infrared light sources may be incorporated in the robotic arm 106, the surgical instrument 104, the laparoscopic port 130, or may be disposed anywhere in the surgical environment.

Figure 2A:
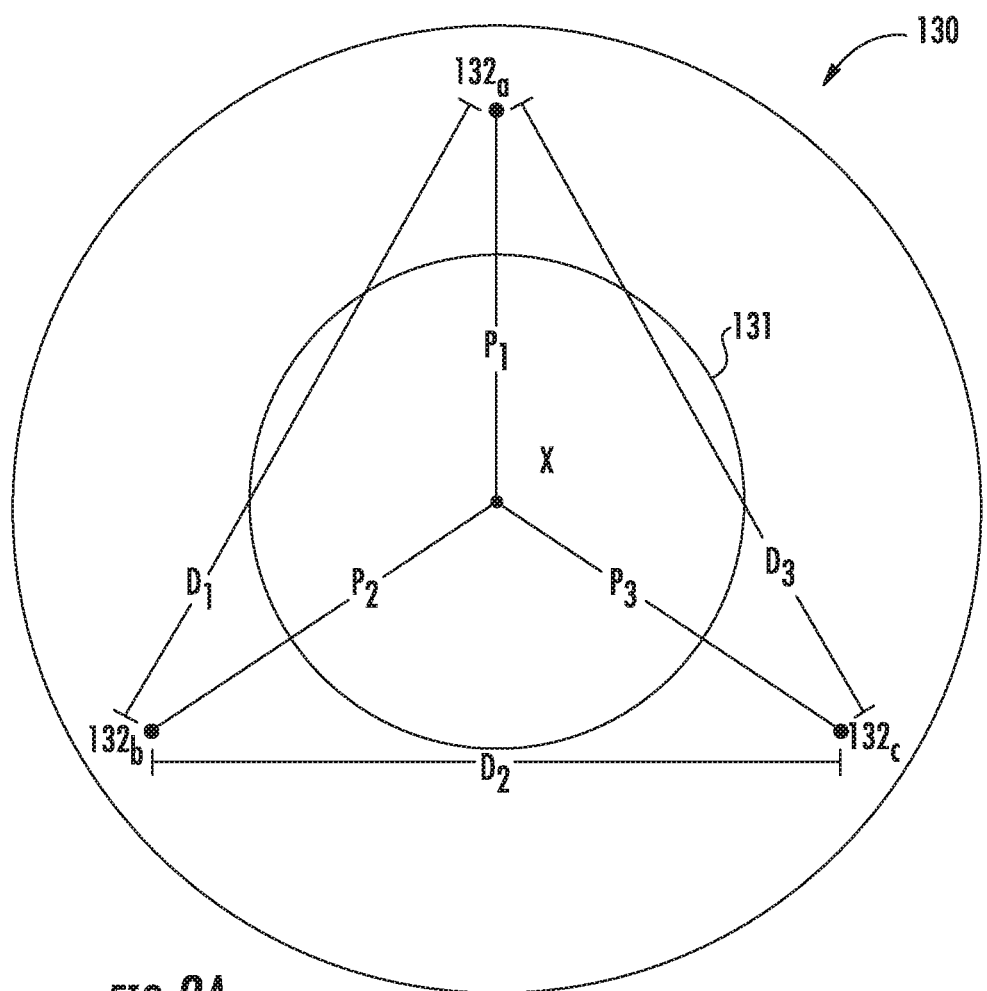
FIG. 2A is a top view of a laparoscopic port in accordance with the present disclosure.

With reference to FIG. 2A, the laparoscopic port 130 has at least three (3) port fiducials 132a-c positioned in a port plane about a port opening 131 of the laparoscopic port 130. The port plane may be defined by an outer surface 133 (FIG. 3A) of the laparoscopic port 130. The port fiducials 132a-c are positioned about the port opening 131 with distances $D_{1-3}$ between the port fiducials 132a-c and distances $P_{1-3}$ between the port fiducials 132a-c and a center "X" of the port opening 131 being known.

Figure 2B:
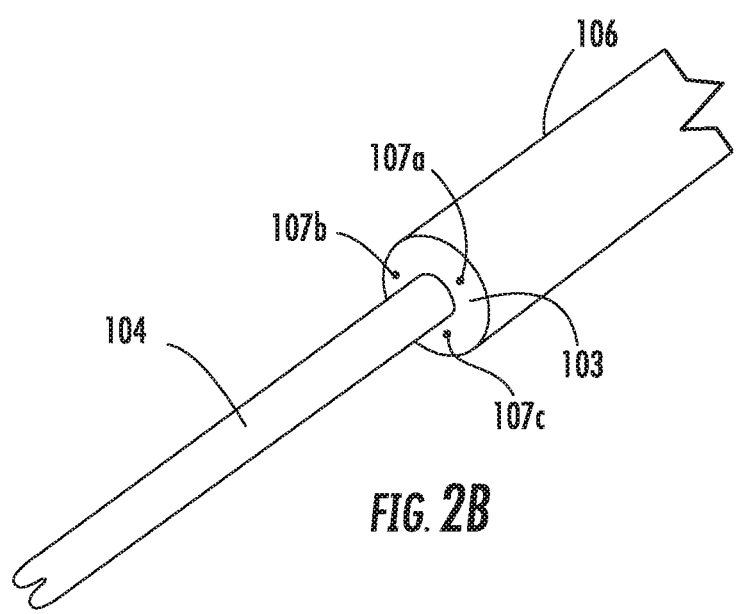
FIG. 2B is a perspective view of a portion of robotic arm of the robot system of FIG. 1 with a surgical instrument attached to the robotic arm.

Referring to FIG. 2B, the robotic arm 106 has at least three (3) arm fiducials 107a-c positioned in an arm plane orthogonal to a longitudinal axis of the robotic arm 106. The arm plane may be defined by a distal surface 103 of the robotic arm 106. Similar to the port fiducials 132a-c, distances between the arm fiducials 107a-c and distances between each of the arm fiducials 107a-c and the longitudinal axis of the robotic arm 106 are known.

Figure 3A:
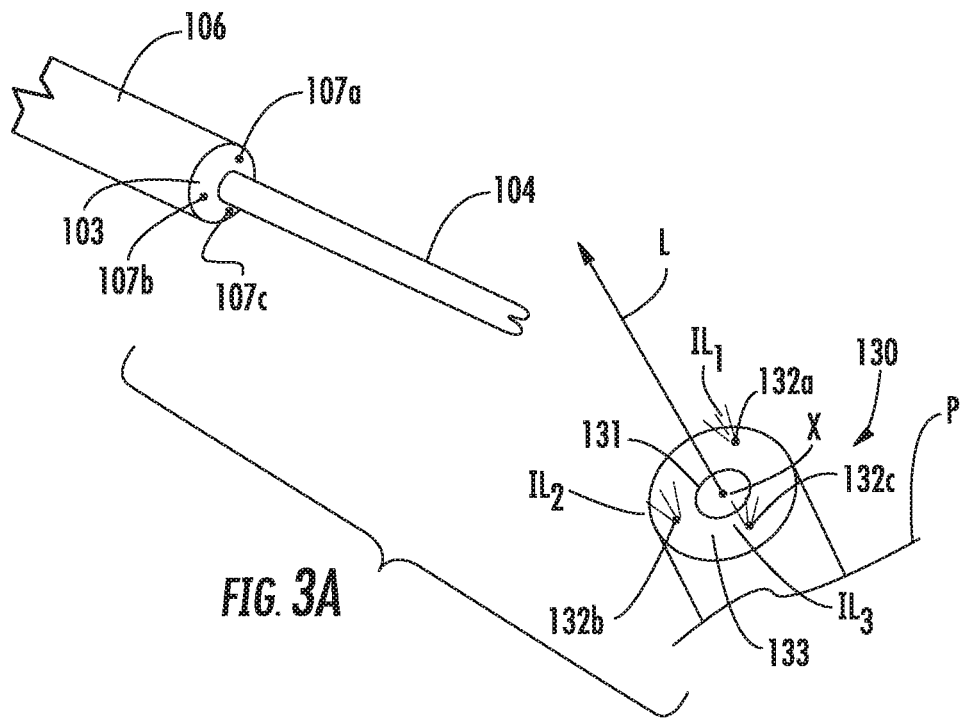
FIG. 3A is a perspective view of an exemplary outside-looking-in optical system in accordance with the present disclosure.

Turning to FIG. 3A, an outside-looking-in optical system is shown according to an embodiment of the present disclosure including the robotic arm 106 and the laparoscopic port 130. In such an embodiment, the port fiducials 132a-c of laparoscopic port 130 are infrared light sources (e.g., active infrared light emitting diodes (LEDs)) which each emit infrared light $IL_{1-3}$ having a distinctive characteristic (e.g., wavelength, phase) and the arm fiducials 107a-c are infrared sensors (e.g., infrared cameras) in communication with the transceiver 118 (FIG. 1). The arm fiducials 107a-c determine the time it takes for infrared light (e.g., $IL_{1-3}$) from the port fiducials 132a-c to reach the respective arm fiducial 107a-c and provides a signal indicative of the time to motion analysis unit 124.

Figure 3B:
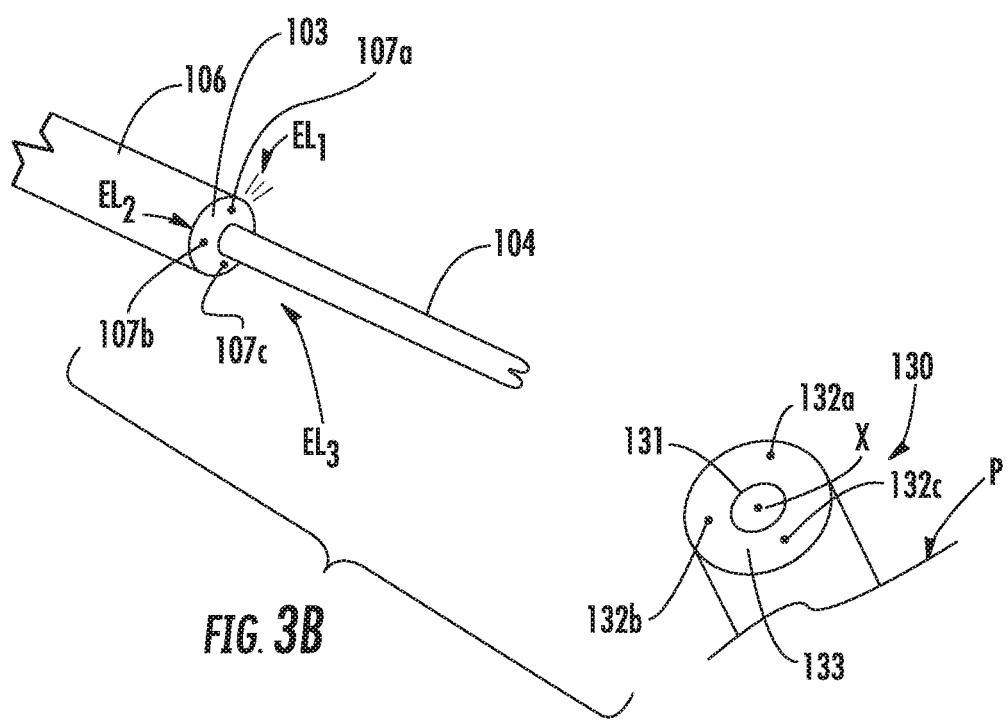
FIG. 3B is a perspective view of an exemplary inside-looking-out optical system in accordance with the present disclosure.

Referring to FIG. 3B, an inside-looking-out optical system is shown according to an embodiment of the present disclosure including the robotic arm 106 and the laparoscopic port 130. The at least three (3) arm fiducials 107a-c are infrared light sources (e.g., active infrared light emitting diodes (LEDs)) which each emit infrared light $EL_{1-3}$ having a distinctive characteristic (e.g., wavelength, phase) and the at least three (3) of laparoscopic port 130 are infrared sensors (e.g., infrared cameras) in communication with the transceiver 118 (FIG. 1). The port fiducials 132a-c determine the time it takes for the infrared light (e.g., $EL_{1-3}$) from the arm fiducials 107a-c to reach the respective port fiducial 132a-c and provides a signal indicative of the motion analysis unit 124.

Figure 3C:
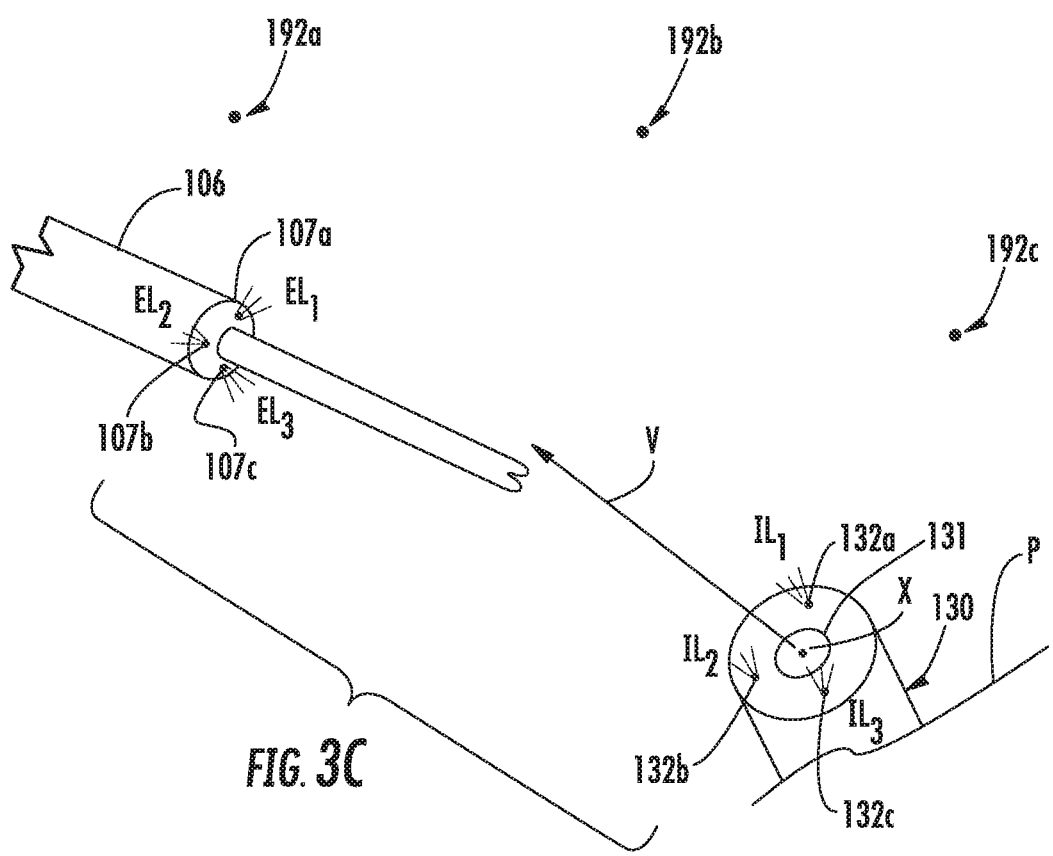
FIG. 3C is a perspective view of an exemplary optical system in accordance with the present disclosure including sensors disposed about an operating theater.

Referring to FIG. 3C, a fixed optical system is shown according to an embodiment of the present disclosure including the robotic arm 106 and the laparoscopic port 130. In such an embodiment, at least three (3) infrared sensors 192a-c (e.g., infrared cameras) are positioned about the operating theater and are in communication with the transceiver 118 (FIG. 1). The port fiducials 132a-c of laparoscopic port 130 are infrared light sources (e.g., active infrared light emitting diodes (LEDs)) which each emit infrared light $IL_{1-3}$ having a distinctive characteristic (e.g., wavelength, phase) and the arm fiducials 107a-c and the arm fiducials 107a-c are infrared light sources (e.g., active infrared light emitting diodes (LEDs)) which each emit infrared light $EL_{1-3}$ having a distinctive characteristic (e.g., wavelength, phase). The positions of the infrared sensors 192a-c within the operating theater are known such that the position of the arm and port fiducials 107a-c, 132a-c relative to the infrared sensors 192a-c can be determined as detailed below. The infrared sensors 192a-c determine the time it takes for infrared light (e.g., $IL_{1-3}$ or $EL_{1-3}$) from the arm fiducials 107a-c and the port fiducials 132a-c to reach the respective infrared sensor 192a-c and provides a signal indicative of the time to motion analysis unit 124.

Figure 4:
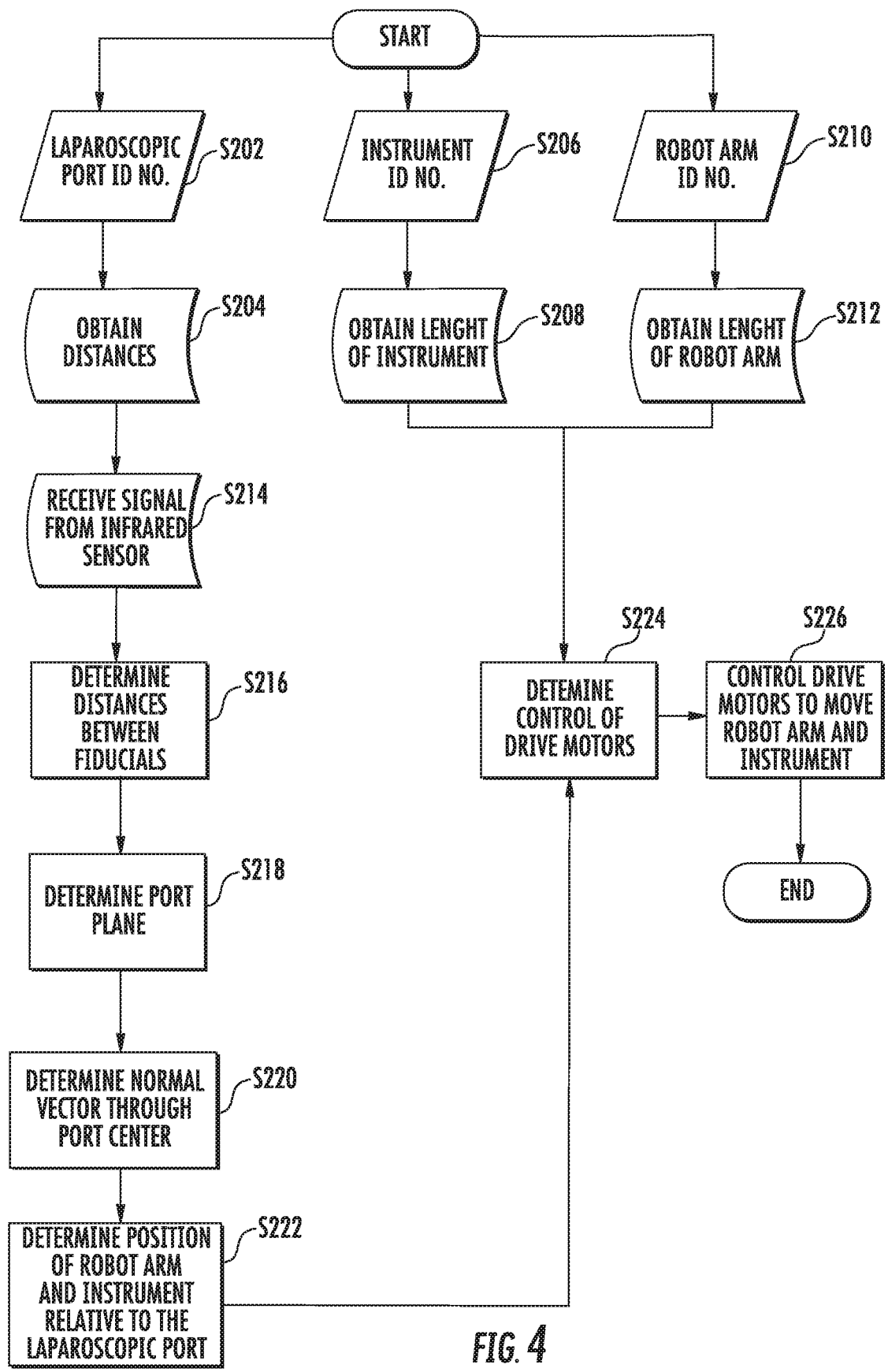
FIG. 4 is a flowchart depicting operation of an automated guidance system of the present disclosure including an optical system of FIG. 3A, 3B, or 3C.

As detailed below with reference to FIG. 4, the motion analysis unit 124 (FIG. 1) determines the position of the robotic arm 106 relative to the laparoscopic port 130 based on signals from the fiducials 107a-c, 132a-c. FIG. 4 will be described while making references to FIGS. 1-3A. As shown in FIG. 4, a user enters a laparoscopic port identification number in step s202. Based on the laparoscopic port identification number, the motion analysis unit queries the memory 126 in step s204 to obtain the distances between port fiducials 132a-c ($D_1$, $D_2$, and $D_3$ as shown in FIG. 2A) and the distances between each port fiducial 132a-c and the port center "X" of the port opening 131 ($P_1$, $P_2$, and $P_3$ as shown in FIG. 2A) that correspond to the laparoscopic port 130. In step s206, an instrument identification number is obtained. The instrument identification number of an instrument 104 coupled to the robotic arm 106 may be obtained via a user input or it may be obtained from an integrated circuit (IC) included in the instrument 104. In step s208, the length of the instrument 104 is obtained based on the instrument identification number, either from the memory 124 or the IC included in the instrument 104. In step s210, a robot arm identification number is obtained. The robot arm identification number may be obtained via a user input or it may be obtained from an IC included in the robot arm 106. In step s212, the geometry of the robot arm 106 is obtained based on the robot arm identification number, either from memory 124 or the IC included in the robot arm 106.

In step s214, the motion analysis unit 124 receives signals from the arm fiducials 107a-c representing the time that the respective infrared light (e.g., $IL_{1-3}$) from a respective one of the port fiducials 132a-c reached a respective arm fiducial 107a-c. Based on the signals from the arm fiducials 107a-c, the motion analysis unit 124 uses three-dimensional spherical trilateration to determine the distance between each of the port fiducials 132a-c and each of the arm fiducials 107a-c in step s216.

For a detailed discussion of three-dimensional spherical trilateration used to determine the location of points in three dimensions, reference can be made to MURPHY JR., WILLIAM S. & HEREMAN, WILLY, DETERMINATION OF A POSITION IN THREE DIMENSIONS USING TRILATERATION AND APPROXIMATE DISTANCES, Nov. 28, 1999, available at http://inside.mines.edu/~whereman/papers/Murphy-Hereman-Trilateration-1995.pdf, the entire contents of which are hereby incorporated by reference.

In step s218, the distances between each of the port fiducials 132a-c relative to each of the arm fiducials 107a-c, the port plane defined by the port fiducials 132a-c is determined relative to the arm fiducials 107a-c.

It will be appreciated that the at least three port fiducials (e.g., port fiducials 132a-c) are required to define the port plane relative to the arm fiducials 107a-c which can be determined as follows:

1. Solving for the vector from 132a, 132b and the vector from 132a, 132c as follows:

$$\vec{AB} = (x_B - x_A)\vec{i} + (y_B - y_A)\vec{j} + (z_B - z_A)\vec{k}$$

$$\vec{AC} = (x_C - x_A)\vec{i} + (y_C - y_A)\vec{j} + (z_C - z_A)\vec{k}$$

2. Determining the normal vector as follows:

$$\vec{AB} \times \vec{AC} = \begin{bmatrix} \vec{i} & \vec{j} & \vec{k} \\ (x_B - x_A) & (y_B - y_A) & (z_B - z_A) \\ (x_C - x_A) & (y_C - y_A) & (z_C - z_A) \end{bmatrix}$$

3. Determine the equation of the plane from the normal vector as follows:

$$((x_B-x_A)+(x_C-x_A))x+((y_B-y_A)+(y_C-y_A))y+((z_B-z_A)+(z_C-z_A))z+d=0$$

4. Use any known point on the plane to solve for d.

As detailed above, the arm fiducials 107a-c are sensors and the port fiducials 132a-c are light sources. Alternatively, the arm fiducials 107a-c can be light sources and the port fiducials 132a-c can be sensors in communication with the motion analysis unit 124. In addition, as detailed above, the arm and port fiducials 107a-c, 132a-c can be light sources and the sensors 192a-c can be sensors in communication with the motion analysis unit 124.

In addition, during step s218, the motion analysis unit 124 determines the port center "X" on the port plane from the position of the three arm fiducials 107a-c. To determine the port center "X", the motion analysis unit 124 solves the following system of equations:

$$(X_x-X_A)^2+(Y_x-Y_A)^2+(Z_x-Z_A)^2=R_A^2$$

$$(X_x-X_B)^2+(Y_x-Y_B)^2+(Z_x-Z_B)^2=R_B^2$$

$$(X_x-X_C)^2+(Y_x-Y_C)^2+(Z_x-Z_C)^2=R_C^2$$

where $R_{A-C}$ are the distances each port fiduciary 132a-c is from a given one of the arm fiduciaries 107a-c.

In step s220, from the position of the port fiducials 132a-c and the port center "X", a vector "V" normal to the port plane defined by the port fiducials 132a-c and passing through the port center "X" provides the orientation of the port opening 131 relative to the arm fiducials 107a-c.

In step s222, the motion analysis unit 124 determines the current position of the robot arm 106 and the instrument 104 relative to the laparoscopic port 130. To determine the current position of the instrument 104, the motion analysis unit 124 can use inverse kinematics based on the known geometry of links of the robot arm 106, the instrument 104, and measured angles between the links of the robot arm 106.

In step s224, the length of the instrument 104 obtained in step s208, the geometry of the robot arm 106 obtained in steps s212, the location of the laparoscopic port 130 determined in step s220, and the current position of the robot arm 106 (e.g., angles between links) and the instrument 104 determined in step s222 are used to determine how to control the drive motors 114 in order to align the instrument 104 with the vector "V" so that the robot arm 106 and/or instrument 104 may be inserted and/or removed from the laparoscopic port 130. It will be appreciated that by determining the vector "V" relative to the arm fiducials 107a-c the movement of the robot arm 106, and thus instrument 104, are relative to the port fiducials 132a-c. In step s226, the drive motors 114 are controlled to perform insertion and/or removal of the instrument 104.

The embodiments disclosed herein are examples of the disclosure and may be embodied in various forms. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments," which may each refer to one or more of the same or different embodiments in accordance with the present disclosure. A phrase in the form "A or B" means "(A), (B), or (A and B)". A phrase in the form "at least one of A, B, or C" means "(A), (B), (C), (A and B), (A and C), (B and C), or (A, B and C)". A clinician may refer to a surgeon or any medical professional, such as a doctor, nurse, technician, medical assistant, or the like performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

The systems described herein utilize optical or visual motion tracking technology; however, it is envisioned that other motion tracking technologies can be used in place of or in conjunction with the optical motion tracking technologies detailed above including, but not limited to, accelerometer, gyroscopic, ultrasound, magnetic, radio frequency, or other light based (e.g., laser) motion tracking technologies.

Any of the herein described methods, programs, algorithms, or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device.

Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. For instance, any of the augmented images described herein can be combined into a single augmented image to be displayed to a clinician. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A robotic surgical system comprising:
   at least one robot arm;
   at least one instrument coupled to the robot arm;
   a plurality of drive motors configured to drive the at least one robot arm;
   a laparoscopic port;
   a plurality of fiducials;
   a plurality of sensors configured to detect the plurality of fiducials; and
   a controller configured to control the plurality of drive motors, the controller including a processor configured to:
      determine a current distance between each sensor of the plurality of sensors and each fiducial of the plurality of fiducials;
      determine a port plane based on the distance between the each sensor and each fiducial;
      determine a vector normal to the port plane passing through a center of the laparoscopic port based on the distance between each sensor and each fiducial;
      determine a position of the at least one robot arm and the at least one instrument relative to the vector; and
      control the plurality of drive motors to align the at least one robot arm or the at least one instrument with the vector.

2. The robotic surgical system of claim 1, wherein the processor is also configured to:
   obtain a predetermined distance between each fiducial among the plurality of fiducials; and
   obtain a predetermined distance between each fiducial and the center of the laparoscopic port.

3. The robotic surgical system of claim 2, wherein the processor determines the port plane based on the current distance between each fiducial among the plurality of fiducials, the predetermined distance between each fiducial among the plurality of fiducials, and the predetermined distance between each fiducial and the center of the laparoscopic port.

4. The robotic surgical system of claim 3, wherein the processor is configured to obtain a length of the at least one instrument.

5. The robotic surgical system of claim 4, wherein the processor is configured to obtain a geometry of the at least one robot arm.

6. The robotic surgical system of claim 5, wherein controlling the plurality of drive motors is based on the position of the at least one robot arm and the at least one instrument relative to the vector, the length of the at least one instrument, and the geometry of the at least one robot arm.

7. The robotic surgical system of claim 1, wherein the plurality of fiducials are active light emitting diodes.

8. The robotic surgical system of claim 1, wherein the plurality of sensors are disposed on the robot arm.

9. The robotic surgical system of claim 1, wherein the plurality of fiducials are disposed on the laparoscopic port.

10. The robotic surgical system of claim 1, wherein the plurality of fiducials are disposed on the robot arm.

11. The robotic surgical system of claim 1, wherein the plurality of sensors are disposed on the laparoscopic port.

12. The robotic surgical system of claim 1, wherein the plurality of drive motors are configured to drive the at least one instrument.

13. A method for guiding a robot arm and/or instrument toward a laparoscopic port, the method comprising:
   determining a position of each fiducial among a plurality of fiducials disposed around the laparoscopic port;
   determining a port plane of the laparoscopic port based on the position of each fiducial;
   determining a vector normal to the port plane passing through a center of the laparoscopic port based on the position of each fiducial;
   determining a position of the robot arm and the instrument relative to the vector; and
   controlling a plurality of drive motors associated with the robot arm and the instrument to align the robot arm or the instrument with the vector.

14. The method of claim 13, further comprising:
   obtaining a predetermined distance between each fiducial among the plurality of fiducials; and
   obtaining a predetermined distance between each fiducial and the center of the laparoscopic port.

15. The method of claim 14, further comprising determining the vector based on the position of each fiducial among the plurality of fiducials, the predetermined distance between each fiducial among the plurality of fiducials, and the predetermined distance between each fiducial and center of the laparoscopic port.

16. The method of claim 15, further comprising obtaining a length of the instrument.

17. The method of claim 16, further comprising obtaining a length of the robot arm.

18. The method of claim 17, wherein controlling the plurality of drive motors is based on the position of the robot arm and the instrument relative to the vector, the length of the instrument, and the length of the robot arm.

19. The method of claim 13, wherein determining the position of each fiducial among a plurality of fiducials includes determining a distance between each sensor of a plurality of sensors and each fiducial of the plurality of fiducials.

* * * * *